United States Patent
Miyazaki et al.

(10) Patent No.: US 9,301,708 B2
(45) Date of Patent: *Apr. 5, 2016

(54) EFFICIENT MULTI-STATION MRI

(71) Applicant: TOSHIBA MEDICAL SYSTEMS CORPORATION, Otawara-Shi, Tochigi-Ken (JP)

(72) Inventors: Mitsue Miyazaki, Des Plaines, IL (US); Katsumi Nakamura, Fukuoka-Ken (JP); Akiyoshi Yamamoto, Fukuoka-Ken (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/857,231

(22) Filed: Apr. 5, 2013

(65) Prior Publication Data

US 2013/0225976 A1    Aug. 29, 2013

Related U.S. Application Data

(62) Division of application No. 13/098,805, filed on May 2, 2011, now Pat. No. 9,157,979.

(51) Int. Cl.
*A61B 5/055* (2006.01)
*G01R 33/567* (2006.01)
(Continued)

(52) U.S. Cl.
CPC .............. *A61B 5/0555* (2013.01); *A61B 5/055* (2013.01); *G01R 33/543* (2013.01); *G01R 33/5673* (2013.01); *G01R 33/56383* (2013.01); *G01R 33/5635* (2013.01)

(58) Field of Classification Search
CPC ............ G01R 33/543; G01R 33/5635; G01R 33/56383; G01R 33/5673; A61B 5/055; A61B 5/0555

USPC ........................ 600/410, 411, 415; 700/19, 90
See application file for complete search history.

(56) References Cited

U.S. PATENT DOCUMENTS 6,946,836 B2   9/2005  Kuhara
7,009,396 B2   3/2006  Zhu et al.
(Continued)

FOREIGN PATENT DOCUMENTS

JP    H01-091842 A    4/1989
JP    2008-302096 A   12/2008
(Continued)

OTHER PUBLICATIONS

M. Miyazaki, et al., "Non-Contrast-Enhanced MR Angiography Using 3D ECG-Synchronized Half-Fourier Fast Spin Echo," *J. Mag. Res. Imaging*, vol. 12, pp. 776-783 (2000).
(Continued)

*Primary Examiner* — Ruth S Smith
(74) *Attorney, Agent, or Firm* — Nixon & Vanderhye P.C.

(57) ABSTRACT

A magnetic resonance imaging (MRI) system includes at least one controller configured to first acquire at least MRI locator image data for different portions of patient anatomy at each of different imaging stations for a defined multi-station locator sequence. An operator may interface with a respectively corresponding displayed locator image for each imaging station to set diagnostic scan sequence parameters for subsequent diagnostic MRI scans of corresponding portions of patient anatomy. Diagnostic MRI scan data is automatically acquired at each of the imaging stations in a multi-station diagnostic scan sequence that, if desired, can be seamlessly continued without operator interruption once begun.

4 Claims, 4 Drawing Sheets

(51) Int. Cl.
*G01R 33/54* (2006.01)
*G01R 33/563* (2006.01)

(56) References Cited

U.S. PATENT DOCUMENTS

| | | | |
|---|---|---|---|
| 7,020,844 | B2 | 3/2006 | Trevino et al. |
| 7,821,267 | B2 | 10/2010 | Yatsui et al. |
| 8,577,442 | B2 | 11/2013 | Miyazaki |
| 2005/0033158 | A1 | 2/2005 | Vu |
| 2007/0225588 | A1 | 9/2007 | Steckner |
| 2010/0249574 | A1 | 9/2010 | Miyazaki |
| 2011/0156704 | A1 | 6/2011 | Boernert et al. |

FOREIGN PATENT DOCUMENTS

| | | |
|---|---|---|
| JP | 2009-160052 A | 7/2009 |
| JP | 2009-072369 | 9/2009 |
| JP | 2009-273929 A | 11/2009 |
| JP | 2010-110510 A | 5/2010 |
| JP | 2010-220859 A | 10/2010 |
| JP | 2011-067696 A | 4/2011 |
| WO | 2010/113062 A1 | 10/2010 |

OTHER PUBLICATIONS

M. Miyazaki, et al., "Peripheral MR Angiography: Separation of Arteries From Veins With Flow-Spoiled Gradient Pulses in Electrocardiography-Triggered Three-Dimensional Half-Fourier Fast Spin-Echo Imaging," *Radiology*, vol. 227, No. 3, pp. 890-896 (2003).

A. Ono, et al., "Deep Vein Thrombosis Using Non-Contrast-Enhanced MR Venography With Electrocardiographically-Gated Three-Dimensional Half-Fourier FSE: Preliminary Experience," *Mag. Reson. Med.*, vol. 61, pp. 907-917 (2009).

Office Action dated Dec. 29, 2014 in U.S. Appl. No. 13/098,805.

EFFICIENT MULTI-STATION MRI

CROSS-REFERENCE TO RELATED APPLICATION

This is a division of copending U.S. Ser. No. 13/098,805 filed May 2, 2011, the entire content of which is hereby incorporated by reference in this application.

FIELD

The subject matter below relates generally to magnetic resonance imaging (MRI) processes. Preferably, the MRI processes described below involve enhancements to multi-station MRI data acquisition workflow.

DETAILED DESCRIPTION

Figure 1:
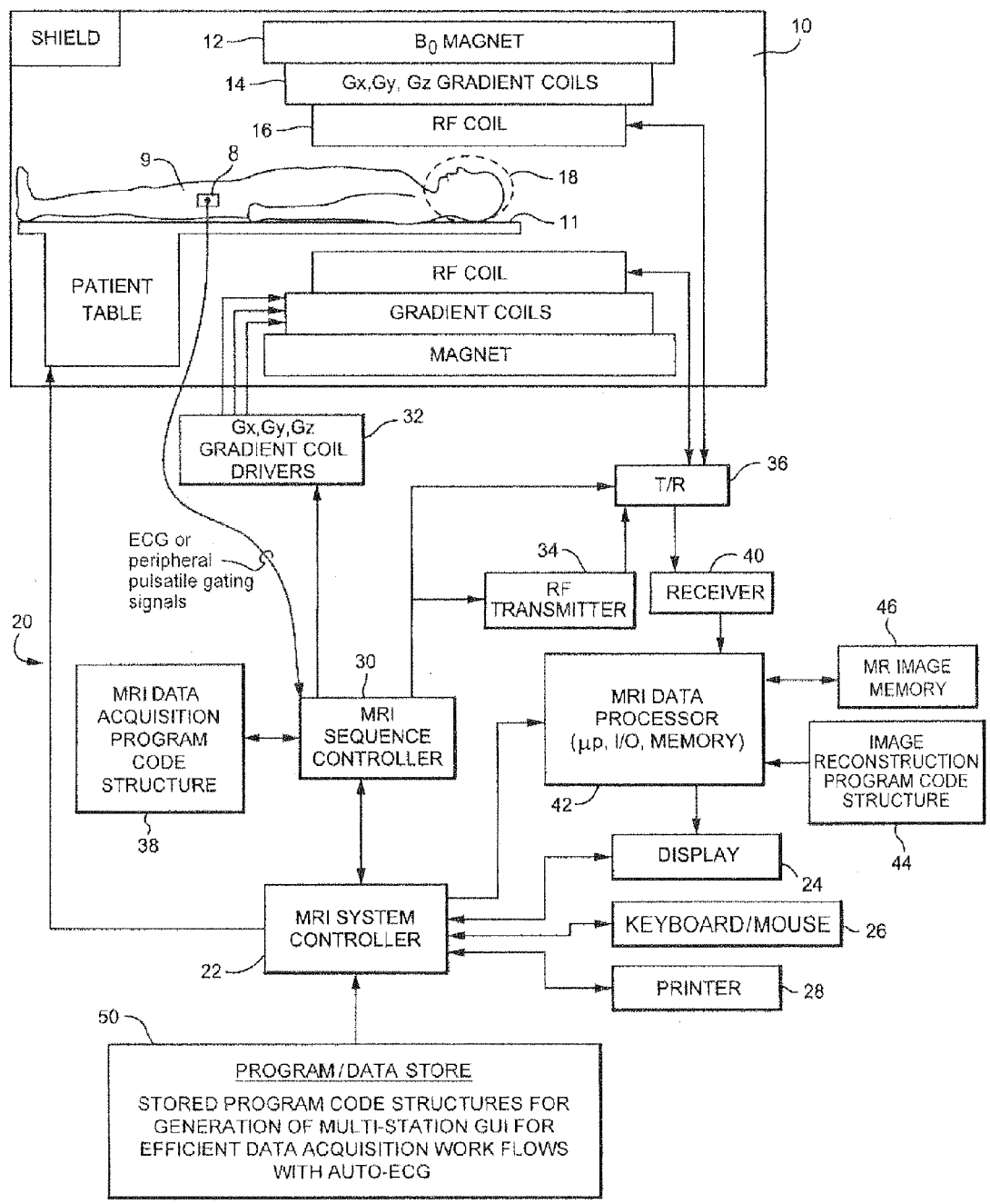
FIG. 1 is a high-level schematic block diagram of an exemplary MRI system embodiment adapted to acquire and process data for MRI using more efficient workflows when acquiring multi-station MRI data.

The MRI system shown in FIG. 1 includes a gantry 10 (shown in schematic cross-section) and various related system components 20 interfaced therewith. At least the gantry 10 is typically located in a shielded room. One MRI system geometry depicted in FIG. 1 includes a substantially coaxial cylindrical arrangement of the static field B0 magnet 12, a $G_x$, $G_y$ and $G_z$ gradient coil set 14 and an RF coil assembly 16. Along the horizontal axis of this cylindrical array of elements is an imaging volume 18 shown as substantially encompassing the head of a patient 9 supported by a patient bed or table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the $G_x$, $G_y$ and $G_z$ gradient coil drivers 32, as well as the RF transmitter 34 and the transmit/receive switch 36 (if the same RF coil is used for both transmission and reception). As those in the art will appreciate, one or more suitable body electrodes 8 may be affixed to the patient's body to provide ECG (electrocardiogram) and/or peripheral pulsatile gating signals to the MRI sequence controller 30. The MRI sequence controller 30 also has access to suitable program code structure 38 for implementing MRI data acquisition sequences already available in the repertoire of the MRI sequence controller 30—e.g., to generate non-contrast MRA (magnetic resonance angiography) and/or MRV (magnetic resonance venography) images using operator and/or system inputs defining particular MRI data acquisition sequence parameters.

The MRI system 20 includes an RF receiver 40 providing input to data processor 42 so as to create processed image data to display 24. The MRI data processor 42 is also configured for access to image reconstruction program code structure 44 and to MR (magnetic resonance) image memory 46 (e.g., for storing MR image data derived from processing in accordance with the exemplary embodiments and the image reconstruction program code structure 44).

Also illustrated in FIG. 1 is a generalized depiction of an MRI system program/data store 50 where stored program code structures (e.g., for generation of multi-station MR images such as non-contrast MRA and/or MRV images for the iliac, femoral and calf anatomies, operator inputs to same, etc.) are stored in computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those in the art will appreciate, the FIG. 1 depiction is a very high-level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR-imaging reconstruction process, an array of computer-readable accessible data value storage sites (e.g., multi-digit binary representations of pixel values) in physical storage media will be transformed from some prior state (e.g., all uniform "zero" values or all "one" values) to a new state wherein the physical states at the physical sites of such an array (e.g., of pixel values) vary between minimum and maximum values to represent real world physical events and conditions (e.g., the tissues of a patient over an imaged volume space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to acquire and/or process MRI data acquisitions and/or to generate and display MR images.

Typically, workflow for multi-station MRI completes all preparatory processes as well as diagnostic scanning at a given station before moving on to the next imaging station. For example, in the typical iliac→femoral→calf sequence, at the first iliac imaging station, both preparatory procedures and diagnostic scan procedures are performed before moving on to the next (e.g., femoral anatomy) imaging station where, once again, all of the preparatory processes are performed as well as the diagnostic scan procedures before moving on to the next successive imaging station (e.g., the calf anatomy). Of course, the same imaging stations may also sometimes be addressed in the reverse order (i.e., calf→femoral→iliac).

Typically, during preparatory scan procedures, well known locator imaging (e.g., using a short gradient echo sequence for a couple of slices), MAP image acquisition (to determine individual RF coil sensitivity coverage of the anatomy to be imaged if parallel imaging is to be performed using an array of RF coils), B0 shimming map image acquisition, electrocardiograph (ECG) related imaging and related analysis of ECG triggering times, etc., are performed. Of course, only after such preparatory procedures is a real diagnostic scan (e.g., a three-dimensional MRI process covering that particular region of the patient's anatomy) performed. Typically, operators determine the ECG or peripheral pulsatile gating (PPG) trigger delay times suitable for matching the patient's systole and diastole cardiac phases that are thereafter applied during three-dimensional diagnostic MRI scans (e.g., for fresh blood imaging (FBI) scans). However, even when the preparatory procedure immediately precedes the diagnostic scan procedures for a given portion of anatomy at a given imaging station, the systolic and/or diastolic delay times may change during the diagnostic scan—which, of course, adversely affects the quality of the resulting diagnostic image. Furthermore, the operator-determination of systole and diastole triggering delay times itself contributes to an increased total examination time.

In peripheral anatomy FBI, it is typical to acquire locator, ECG-prep or phase contrast (PC) for peak flow images, from which the operator can determine systolic and diastolic trigger delays and, eventually, then acquire three-dimensional FBI (systolic and diastolic scans). Typically, this was repeated for three or four stations or so (e.g., the successive patient anatomies of aorto-iliac, femoral, calf, foot, etc.). Not only does this require time, it also requires operator experience due to the complexity of the several data acquisitions required to determine proper cardiac phase delay times and the like.

Although there are by now also auto-ECG functions available for automatically determining systolic and diastolic triggering delay times (e.g., directly from an electrocardiograph signal without requiring acquisition of an ECG-prep scan), such have apparently not previously been used for multi-station FBI image acquisitions.

For more information concerning FBI and auto-ECG techniques, reference may be had to published application US 2010/0249574 A1. Among other things, it will be noted therein (e.g., see paragraphs [0043]-[0065]) that automatically determined systole and/or diastole time periods need to be adjusted so as to properly correspond to each different region (e.g., iliac, femoral and calf). The delay in MRI sequence trigger times may vary over a wide range as distance from the patient's heart and/or blood flow velocity vary. Delayed trigger time (e.g. elapsed time from an ECG R-wave to initiation of a MR imaging data acquisition scan sequence) may automatically be adjusted as one images different body portions having different cardiac cycle characteristics. The auto-ECG timing may also be affected by the time difference between an ECG signal and a PPG signal acquired from a distal body portion such as a finger or hand and/or a difference in average blood flow velocities.

The FBI method is a non-contrast-enhanced MRA method used to acquire echo data repeatedly during successive heartbeat cycles while delaying MRI sequence triggering by a predetermined delay time from an ECG trigger signal synchronized with a reference portion of an ECG wave, such as an R wave. Each delay represents a cardiac time phase of a patient using an SE (spin echo) series MRI sequence such as an SSFP sequence and an FASE (fast asymmetric spin echo or fast advanced spin echo) sequence that uses the half-Fourier method. According to the exemplary FBI method, a transverse relaxation (T2) component of magnetization in blood is recovered over plural heart cycles and a water (blood) weighted image in which the T2 magnetization component of blood is enhanced can be obtained as a blood vessel image. In the FBI method, a three-dimensional scan for acquiring echo data (volume data) for predetermined slice encode amounts is performed. For example, in the case of imaging under the FBI method, arteriovenous-separated blood flow image data can be generated with favorable contrast by acquisition of pieces of data in a systole and a diastole phase, respectively, over plural heart cycles by an SSFP sequence or an FASE sequence and then using subtraction processing between the acquired diastole and systole image data sets.

Heart rate acquisition in an imaging condition setting unit functions to acquire ECG heart rate information of a patient from an ECG unit or a PPG unit and this provides heart rate (HR) and ECG data of the patient to a delay time setting process. The acquired heart rate information includes the HR itself and the time period between adjacent reference waves in an ECG signal (or a PPG signal), as well as the ECG signal (or PPG signal). When the ECG unit or the PPG unit functions to calculate HR, a heart rate acquisition module can be configured to acquire HR from the ECG unit or the PPG unit directly. The heart rate acquisition module may also be configured to acquire an ECG signal, a PPG signal or the period between adjacent reference waves on an ECG or PPG signal from the ECG unit or the PPG unit and to calculate HR based on the EGG signal or the PPG signal.

Note that the heart rate acquisition module may also be configured to calculate or acquire plural HRs and to provide an average value of the plural HRs to the delay time setting module for accuracy improvement. For example, the heart rate acquisition module may acquire a HR around ten different times and use the average value of the ten HRs as the HR provided to the delay time setting module. For example, one might acquire HR data only four to twenty times in order to calculate an average HR value with practical accuracy.

The delay time setting module functions to set an appropriate delay time from a reference wave as an imaging condition in heart rate synchronous imaging based on the HR acquired from the heart rate acquisition module. The setting methods for a delay time include a method of calculating a delay time from HR using a calculating formula representing a relationship between HR and delay time and a method of preparing a table showing relationship between HRs and delay times to acquire a delay time corresponding to a HR of a patient in reference to the table.

An imaging region for a blood flow image can also be set arbitrarily. Therefore, an imaging condition for blood flow imaging of a lower limb or coronary artery imaging can be set. However, blood flow velocity is different depending on the imaged part. Therefore, an appropriate delay time from a reference wave of ECG data acquisition timing may also desirably be set with a higher accuracy as a different value depending on the imaged part. For that reason, a calculation expression showing a relation between a HR and a delay time can also be set for each different imaging part. For example, since blood flow velocity at a low end portion such as a lower limb is slower compared to that in the vicinity of the heart, a delay time for a low end portion of the body can be set differently than a delay time for an imaged part in the vicinity of the heart. In this case, a delay time can also be determined depending on not only distance from the heart to an imaging location, but also a time difference between an ECG signal and a PPG signal acquired from a distal portion such as a finger of the hand, and/or a difference in average blood flow velocities.

Although exact offset time values may vary, in general the ECG offset time for diastole may be different from that for systole. The ECG offset time for systole may also be smaller than that for diastole. For example, ECG offset time for systole may be zero to tens of msec and ECG offset time for diastole may be an additional 100-200 ms.

The ECG offset time for diastole may be set smaller depending on the location of a particular imaging station. As noted, the systole/diastole offset times for each station may be different values or, in some cases, the offset times for some or all stations may also be the same values.

For example, an ECG offset time for diastole may be on the order of:
 iliac=+150 ms, femoral=+140 ms, calf=+100 ms or
 iliac=+150 ms, femoral=+150 ms, calf=+120 ms, etc.

Suitable formulae may be derived for a given population of body types, imaging stations, cardiac cycle phases, etc. For example, the following formulae may be appropriate for average body types in FBI for the calf, thigh and iliac regions: systolic delay (in ms)=(550−2 HR)/2 and diastolic delay (in ms)=(RR−550+2 HR)/(2+α) where RR=period between two successive R-waves in an ECG signal and a can take on different values for the calf, thigh and iliac regions (e.g., so as to provide different respective values for these different regions as noted just above). As will be understood, HR in milliseconds can be quickly calculated from an R-R interval using the formula RR=60,000/HR or HR=60,000/RR.

As a net result of prior multi-station workflow and/or failure to utilize auto-ECG functionality in the context of multi-station FBI image acquisitions, a typical three-station iliac, femoral, calf FBI scan sequence might typically take on the order of about 40 minutes. However, the total examination time might be reduced by approximately one-half using auto-ECG functionality (e.g., to something on the order of 20 minutes for the same three-station FBI procedure). By also adopting an improved multi-station workflow in accordance with FIG. 2, the total examination time may be further reduced to approximately 15 minutes or less for the same procedure—thus representing a considerable savings in total examination time and a corresponding improvement in MRI system utilization time.

Although the presently preferred exemplary embodiment is presented in the context of non-contrast FBI scans to provide magnetic resonance angiography (MRA) and/or magnetic resonance venography (MRV) images, it may also be applicable to other multi-station MRI procedures as will be apparent to those in the art. For example, TOF (time of flight) MRI is another well known class of angiography (e.g., wherein TOF MRI is based on an ability to distinguish between stationary and flowing MR nuclei).

In the exemplary embodiment, the order of workflow (e.g., head-to-foot or foot-to-head) stations is selectable. Non-contrast FBI scans obtained at multiple imaging stations along extended peripheral anatomy structures (e.g., legs extending from the iliac through the femoral and calf regions of this peripheral anatomy) can be obtained. Here, in accordance with the exemplary workflow sequences depicted in FIG. 2, all of the locator images, information on B1 shimming (if needed), MAP, etc., as may be required during preparatory scan procedures for a given system are first obtained for all of the imaging stations. Thereafter, the actual three-dimensional FBI diagnostic scans are performed (e.g., in reverse or same order sequence) at those same stations using at each station the set-up information previously set based on the preparatory scan data derived for that particular station. The diagnostic scan parameters may be set in a multi-tasking mode possibly starting as early as after the preparatory scan data becomes available from the first station scanned—thus permitting a seamless progression of preparatory and diagnostic scans without operator interruption. Auto-ECG functionality is used, where applicable (e.g., for FBI), during diagnostic scans so as to (a) eliminate the necessity for manual systole/diastole determinations during preparatory procedures, and (b) automatically adapt to on-going changes in the patient's systole/diastole triggering points during actual diagnostic scanning processes (e.g., including automatic adjustments in systole/diastole triggering times as a function of station location vis-à-vis the heart).

If desired, after diagnostic scanning has been completed at a given station, before moving on for diagnostic scanning at the next station, image quality of the just acquired diagnostic scan data can be quickly confirmed by displaying a relatively low resolution image (e.g., for FBI processes, a subtracted systole/diastole MIP (maximum intensity projection)) on the console. The operator can then be given an opportunity to re-acquire new diagnostic image data, if needed (with altered imaging parameters, if desired). Alternatively, all the diagnostic scan data can be automatically acquired at each successive station without stopping for manual review options. Further, as noted above, once the preparatory scans have been initiated, it is possible to proceed seamlessly thereafter through all preparatory scans and diagnostic scans without interrupting the process. For example, if a multi-tasking mode is used, an operator may begin inputting/setting diagnostic scan parameters as soon as possible for a given station (e.g., even during preparatory scans for other stations so that diagnostic scans may begin immediately at any desired time thereafter without the need to wait for operator inputs).

The present exemplary embodiment greatly eases operator workload—especially when auto-ECG functionality and automatic sequencing along multiple imaging stations are utilized for diagnostic scan procedures. The exemplary embodiment also greatly improves the workflow associated with both preparatory and diagnostic scan procedures and, when considered as a whole, tremendously decreases the overall required examination time.

To shorten overall examination time for multiple station imaging (e.g., in the iliac, femoral and calf anatomy regions), all required scans may be systematically and automatically acquired. For example, the system may acquire all locator images from the calf, femoral and iliac anatomies in either desired sequential order (e.g., foot-to-head order or vice versa). This may include multiple directional scans (e.g., axial and/or coronal) while also allowing adjustable gaps in axial and/or coronal imaging so as to permit the operator to more easily determine the desired anatomy coverage and thus enable a proper set up for a desired FBI three-dimensional slab location for each successive anatomy portion. A MAP, B0 shimming information and B1 shimming information (e.g., for three Tesla and above MRI systems) may also be acquired and recorded during these preparatory processes.

After at least one of the preparatory procedures has been completed and the operator has determined desired diagnostic image coverage (e.g., for particular slices and/or three-dimensional slabs), the operator may then review the acquired preparatory data and set diagnostic scan parameters for that scan station. Alternatively, all the preparatory scan data may be acquired before staring to set diagnostic scan parameters and instructing the MRI system to acquire diagnostic data from all of the multiple imaging stations (e.g., possibly in any desired sequence) by activating an appropriate "start" input command. While the preparatory or diagnostic scan at a given station is underway, preparatory data for the remaining stations may continue to be set by the operator, if such settings have not already been completed. Since it typically may take much less time to set the desired diagnostic scan parameters (e.g., perhaps 20 seconds or so) than to perform the diagnostic scan (e.g., perhaps 2+ minutes or so), the ongoing automatic sequential multi-station diagnostic scanning, once started, should not get ahead of the operator. If it does, a short wait loop may be effected until the operator catches up. Alternatively, the operator may set desired diagnostic scan parameters for all stations before the automatic diagnostic scan processes are initiated.

In any event, using set-up data acquired based on the multi-station preparatory scan procedures, the MRI system itself may now automatically proceed from one station to the next to perform appropriate diagnostic scan data acquisitions. On the other hand, if desired, after acquisition of diagnostic imaging data at a given station, a quick low resolution image can be generated and displayed for the operator to quickly review and approve before moving on to the next diagnostic imaging station. If this option is chosen, and if the operator disapproves, then the diagnostic scan may be repeated, using different diagnostic scan parameters if desired, until the operator is satisfied with the acquired diagnostic image data for that particular station before moving on to the next.

As just noted, depending upon required preparatory, set-up and/or diagnostic scan procedures for a given situation, multi-task processes may be employed. For example, while acquiring preparatory or diagnostic scan data in the iliac region, previously derived preparatory scan data acquired for the femoral region may be reviewed and diagnostic scan parameters set for use at the next (i.e., femoral) imaging station. It may also be that to save preparatory scan time, the preparatory scan procedures have not yet conducted and recorded the MAP or other still required further preparatory scan(s). In such case, it is possible to set up automatic subsequent acquisition and substantially immediate use of such data at the current imaging station—now as a brief preparatory part of the diagnostic scan procedures that will be conducted immediately thereafter at that station. If time permits, once such auto-scan parameters are set for one region, multi-tasking may move on to similarly set such parameters for the next station, and so on.

As noted, it may be desired that after FBI images are acquired for a given region (e.g., the iliac region), subtracted MIP images with lower resolution (e.g., 128×128 pixels instead of perhaps $256^2$ or $512^2$ pixels as may be used for a higher resolution diagnostic image) are quickly generated and displayed on a monitor to the operator for agreement on the result before moving on to the next imaging station. If the lower resolution quick images are not acceptable to the operator, then the diagnostic scan data acquisition for that particular region (e.g., the iliac) can be repeated—possibly with changed imaging parameters at operator discretion.

Figure 2:
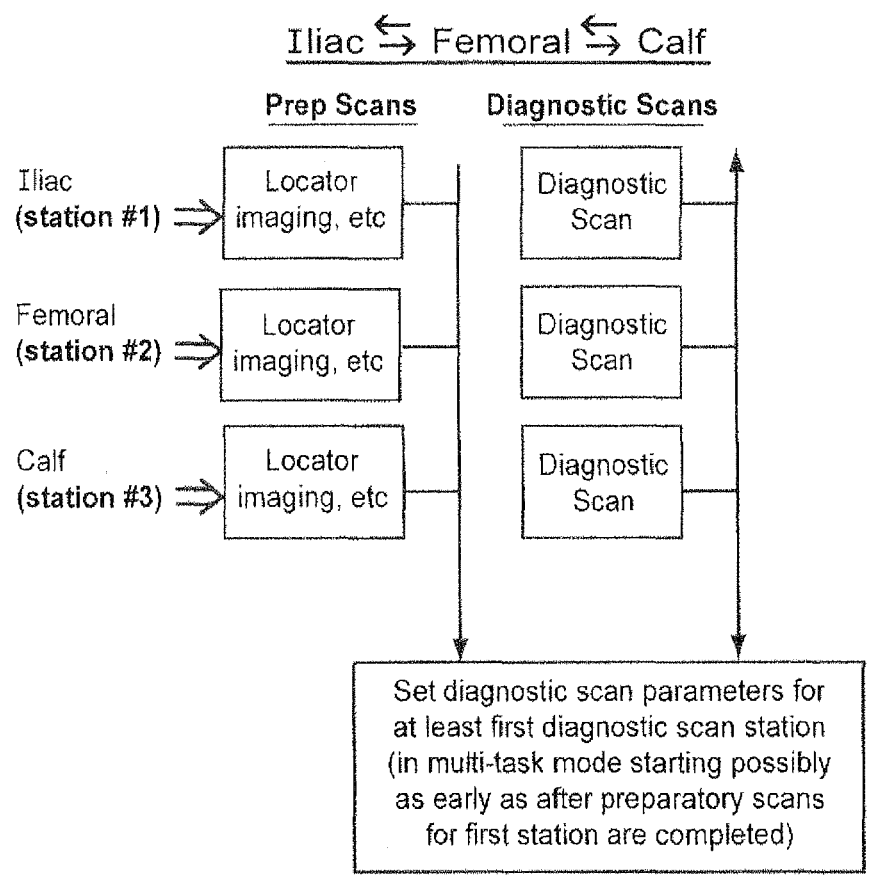
FIG. 2 is a schematic depiction of an exemplary embodiment of improved multi-station workflow sequences.

A preferred graphical user interface (GUI) displays a multiple imaging station region such as depicted in FIG. 2 in an operator observation area (e.g., possibly including relatively small-scale lower resolution images related to each such station workflow). Preferably, when considering acquired preparatory scan data and setting diagnostic scan parameters, the operator may designate and transfer any such observed workflow item to a different "working area" of the display scan, whereupon opportunities are given the operator to set scan conditions such as changing gaps for locator images or the like.

Figure 3:
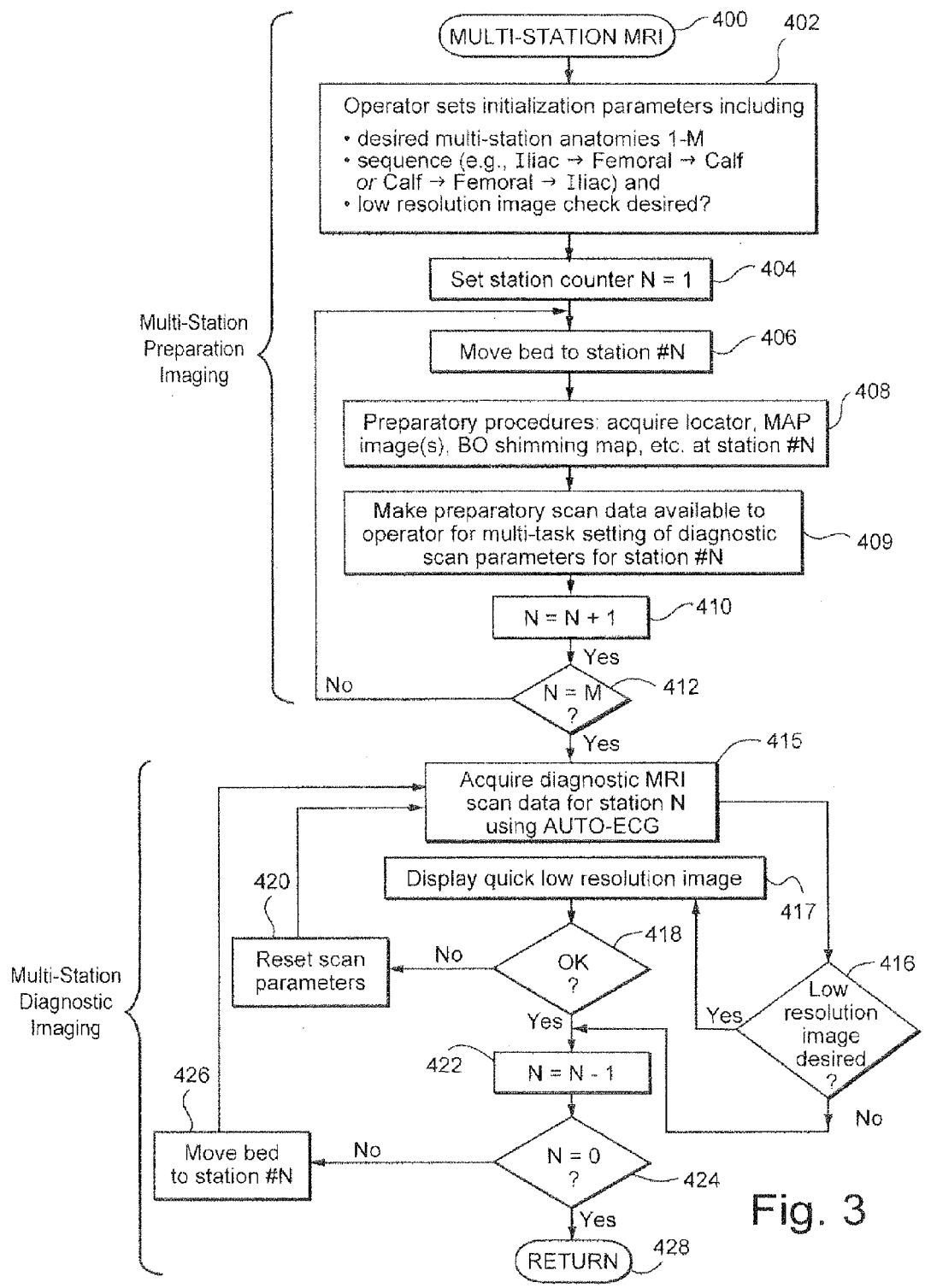
FIG. 3 is a schematic illustration of exemplary computer program code structure in the form of a flow chart for implementing the exemplary workflow sequence depicted in FIG. 2.

An exemplary computer program code structure for implementing the improved workflow of FIG. 2 is depicted at FIG. 3. Here, a multi-station MRI procedure/module is entered at 400. At 402, an opportunity is provided for the operator to set desired initialization parameters such as, for example, desired multi-station anatomies 1-M (e.g., 1-3 corresponding to the iliac, femoral and calf anatomies) as well as the desired workflow sequence (e.g., head-to-foot or foot-to-head) and whether a low resolution image check is desired at a given station before moving on to the next during diagnostic image data acquisition procedures.

After initialization, an imaging station counter N is initialized to a value of one at 404 and the patient bed is then moved so as to position the corresponding patient anatomy within the imaging volume of the MRI system by moving the patient bed to station N at 406. While at this particular imaging station, all desired preparatory processes are preferably performed such as possibly acquiring locator and/or MAP images, B0 shimming map, etc. at 408. Preferably, after being initiated, such preparatory procedures will not require further interactions with the operator so as to permit continuous automatic multi-station sequencing while gathering preparatory scan data. As soon as preparatory scan data becomes available for station N, an opportunity may be presented at 409 so that such data is made available to the operator to begin multi-task data entry, if desired, for setting diagnostic scan parameters for station N (i.e., so that such diagnostic scan parameters are already set and available for use whenever diagnostic scanning for that station is thereafter desired). Then the station counter N is incremented at 410 and tested at 412 to see if all designated stations have been yet prepared. If not, then control is moved back to box 406 where the bed is moved to the next imaging station.

On the other hand, once preparatory scan data for all of the multiple stations have been acquired, then the decision at 412 (which may include an optional operator interface as well as an automatic determination as to whether preparatory scans have been completed), control is then passed to the diagnostic portion of FIG. 3. Here, at 415 diagnostic MRI scan data is acquired for station N (which will initially remain at a value M in this example). As depicted at 415, the auto-ECG functionality will be used for such diagnostic data acquisition so as to reduce operator time and machine time during preparation phases, as well as to automatically adapt to changes in systole/diastole patient cardiac phases during diagnostic imaging. As explained in US 2010/0249574 A1, the systole/diastole trigger times can be automatically adjusted as a function, inter alia, of station position with respect to the patient's heart (e.g., the triggering points for the femoral station will be slightly delayed with respect to the trigger points for the iliac station, etc.).

Once the diagnostic scan data has been acquired at 415, then if the low resolution image flag has been set as tested at 416, a quickly generated low resolution image is displayed at 417 for operator approval. For example, if FBI is employed, then a quick subtraction of systole/diastole images and MIP processing may produce a low resolution 128×128 pixel image for quick display. If the operator disapproves of the preliminary image at 418, then the operator may reset/change diagnostic scan parameters at 420 before control is passed back to box 415 for again acquiring diagnostic MRI scan data for this same station.

Once the operator is satisfied with the quickly displayed low resolution image, or if the low resolution image flag was not set, then control is passed to box 422 where the station counter is now decremented. A test is made at 424 to see if all stations have yet been serviced. If not, then control is passed to box 426 where the patient bed is moved to the next imaging station before control is passed to box 415 for again acquiring diagnostic MRI scan data for this next station.

Finally, after all of the imaging stations have been handled, control will pass from 424 to 428 where a return transfer is made (e.g., to the program routine that initially called the multi-station MRI module 400 into operation).

As those in the art will appreciate, if desired, the sequence of preparatory scans and diagnostic scans may be arbitrarily defined. For example, the preparatory scans may be in the head-to-foot direction and the diagnostic scans may be in either foot-to-head or head-to-foot sequence. Further, the scan station sequences need not be in body anatomy sequence. As will be understood, minor changes to the station counter incrementing, setting decrementing, etc., may result in arbitrary station sequences.

The exemplary GUI allows improvement in operator setting of scanning conditions due to improvement in workflow, as well as shorter scan times to obtain all stations in peripheral anatomy multi-station imaging. The use of calculated ECG or PPG delays using "auto-FBI" during diagnostic imaging allows actual real-time heart rate to be used in the diagnostic scan as compared to acquiring ECG-prep scan(s) and calculation/FBI-Navi functions. Overall scan time is further shortened using auto-FBI in this GUI. In a perhaps optimum implementation, once begun (e.g., by an operator activation of a "begin scan" icon or button), the whole multi-station process is seamless in that the machine operations need never be delayed by interruption for operator actions.

Workflow of non-contrast FBI scans in peripheral anatomy run-offs is improved by the system GUI. Movements of the patient table for acquiring locator and/or shimming information are based on data retained in the system to reapply during actual diagnostic scan conditions. Each station FBI acquisition can be used as a "get interval" function of ECG or PPG to refresh this data each time diagnostic data is acquired, thus providing automatic establishment of diastolic and systolic triggering delays using the "auto-ECG" function. To confirm the image quality of a subtracted MIP diagnostic image, a low resolution subtracted MIP is preferably displayed on the console.

This provides easy operation, faster scanning and more reliable imaging especially for non-contrast MR angiography and MR venography techniques.

The exemplary embodiment reduces total scan time in multiple stations, such as in the iliac, femoral and calf regions, where all scans can be systematically and automatically acquired. The exemplary system acquires all locator images (e.g., from calf, femoral and iliac order (feet-to-head order or reverse order). Multiple directional scans (axial and coronal) with appropriate gaps in the axial and coronal imaging can be executed for locator images, which allow an operator to more easily determine the coverage. While setting up an FBI slab location on the iliac, information of recorded MAP and B0 shimming is applied. After slice coverage is determined by the operator, the operator can simply push a scan button to acquire diagnostic data for the iliac—and this can be automatically continued—or, if desired, repeated for successive anatomies. If four stations are required, the same strategy applies. The order of acquisition can be selected; i.e., instead of lower-to-upper, upper-to-lower order (or any desired arbitrary order) can be effected. In the case of MR venography in the iliac region, three images can be acquired at this station to have non-contrast MR venography.

Figure 4:
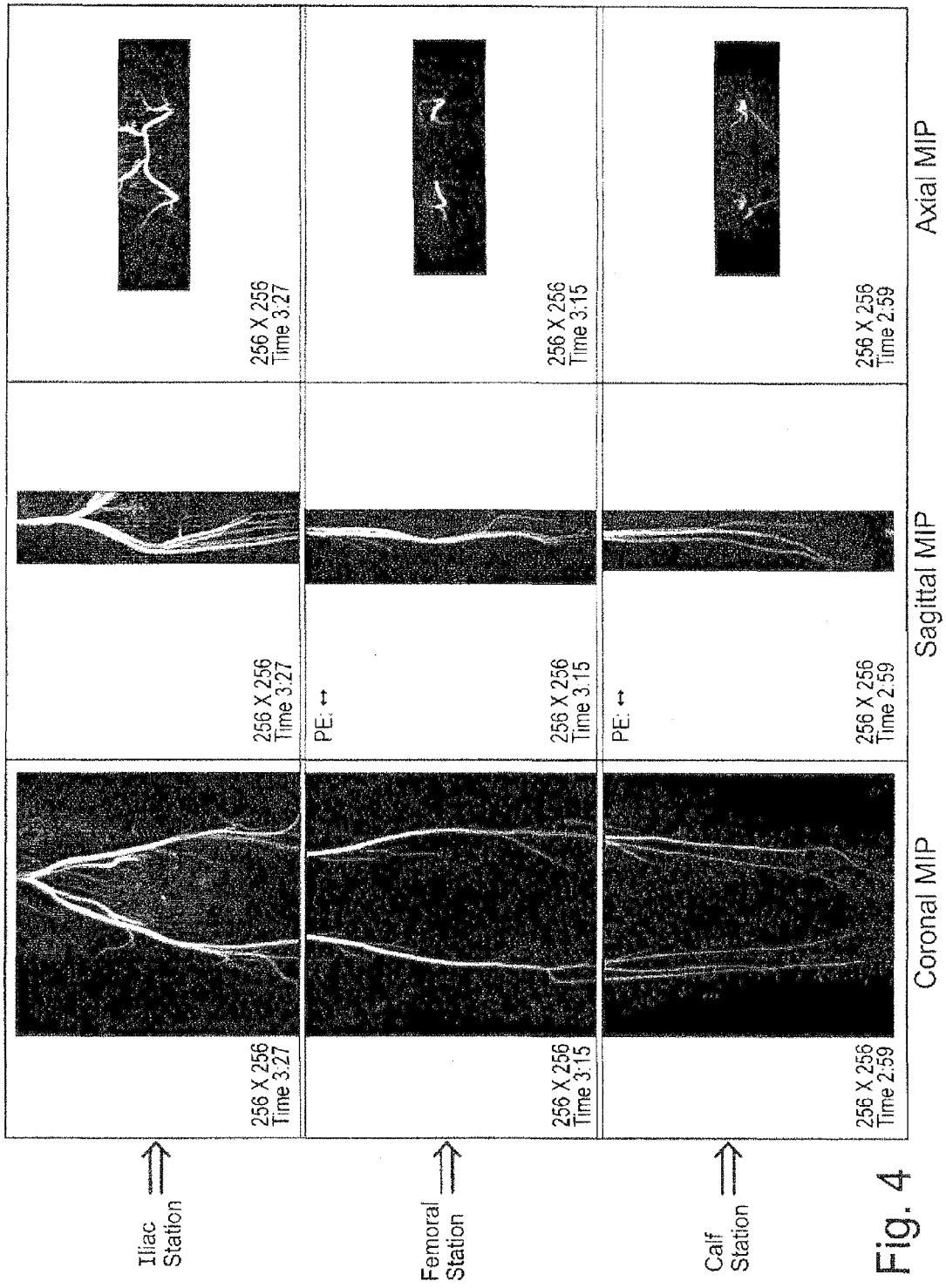
FIG. 4 is a composite collection of Coronal, Sagittal and Axial MIP images from the Iliac, Femoral and Calf stations.

FIG. 4 is a composite collection of coronal, sagittal and axial MIP images from an exemplary iliac, femoral and calf efficient multi-station imaging process showing typical resulting 256×256 resolution images.

While certain embodiments of the inventions have been described, these embodiments have been presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) system comprising:
   an MRI gantry having components including a controllably movable patient bed configured to move a patient, when positioned on the patient bed, along an imaging axis of the gantry to different imaging stations for imaging different portions of the patient's anatomy, when positioned in an imaging volume, in a multi-station MRI mode, and
   a processing system including an MRI system controller, an MRI sequence controller, and an MRI data processor, the processing system being configured to:
      cause the patient bed to be sequentially moved to each of the different imaging stations so that, in turn, each of the different portions of the anatomy is successively positioned within the imaging volume, and
      acquire a heart rate signal from a detected repeating cardiac cycle of the patient, and set a delay time for image data acquisition from a reference time, within said cardiac cycle, at each imaging station based on the acquired heart rate,
      wherein the processing system is further configured to set a first delay time for a first multi-station location within the anatomy to be smaller than a second delay time for a second multi-station location within the anatomy, wherein the first multi-station location is further from a location on the patient bed that corresponds to an anatomy portion including a patient's heart than the second multi-station location.

2. An MRI system as in claim 1, wherein the processing system is further configured to set a first offset time when acquiring image data during diastole of a cardiac cycle of said patient's heart rate signal with respect to the first delay time to be smaller than a second offset time which is used when acquiring image data during diastole of a cardiac cycle of said patient's heart rate signal with respect to the second delay time.

3. A magnetic resonance imaging (MRI) method comprising:
   sequentially moving, in a multi-station MRI mode, a patient bed along an imaging axis in an MRI gantry to each of different imaging stations so as to successively position each of different portions of patient anatomy when positioned on the patient bed within an imaging volume,
   acquiring a heart rate signal from a detected repeating cardiac cycle of the patient; and
   setting a delay time for image data acquisition from a reference time, within said cardiac cycle, at each imaging station based on the acquired heart rate,
   wherein a first delay time is set for a first multi-station location within the patient and a second delay time, larger than said first delay time, is set for a second multi-station location within the patient, wherein the first multi-station location is further from a location on the patient bed that corresponds to an anatomy portion including a patient's heart than the second multi-station location.

4. An MRI method as in claim 3, wherein a first offset time used to acquire image data during diastole of a cardiac cycle of said patient's heart rate signal with respect to the first delay time is set to be smaller than a second offset time used to acquire image data during diastole of a cardiac cycle of said patient's heart rate signal with respect to the second delay time.

* * * * *